United States Patent [19]

Rosenberger

[11] 4,349,445
[45] Sep. 14, 1982

[54] DITHIOPHOSPHATES AS LUBRICANT ANTIOXIDENTS AND ANTI-CORROSION AGENTS

[75] Inventor: Siegfried Rosenberger, Riehen, Switzerland

[73] Assignee: Ciba-Geigy Corporation, Ardsley, N.Y.

[21] Appl. No.: 187,641

[22] Filed: Sep. 15, 1980

[30] Foreign Application Priority Data

Sep. 18, 1979 [CH] Switzerland ............ 8418/79

[51] Int. Cl.³ .................... C10M 1/48; C07C 9/18
[52] U.S. Cl. ................ 252/46.6; 260/953; 260/937
[58] Field of Search ......... 260/953, 931; 252/46.6

[56] References Cited

U.S. PATENT DOCUMENTS

| | | | |
|---|---|---|---|
| 2,976,308 | 3/1961 | Bacon | 260/978 |
| 3,017,422 | 1/1962 | Thompson . | |
| 3,662,033 | 5/1972 | Meltsner | 260/953 |
| 3,745,148 | 7/1973 | Shin et al. . | |
| 4,132,702 | 1/1979 | Schmidt et al. | 260/941 |

FOREIGN PATENT DOCUMENTS 1506917 4/1978 United Kingdom .

Primary Examiner—Anton H. Sutto
Attorney, Agent, or Firm—Luther A. R. Hall

[57] ABSTRACT

Compounds of the formula

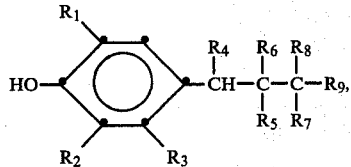

wherein the symbols $R_1$ to $R_9$ have the meanings given in claim 1, are suitable as extreme pressure and antiwear additives in lubricants. The compounds contain as radicals $R_5$ or $R_7$ a group of the formula

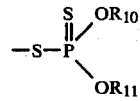

wherein $R_{10}$ and $R_{11}$ have the meanings given in claim 1. The compounds according to the invention are characterized also as good antioxidants and anti-corrosion agents.

9 Claims, No Drawings

DITHIOPHOSPHATES AS LUBRICANT ANTIOXIDENTS AND ANTI-CORROSION AGENTS

The present invention relates to dithiophosphates, to their use as lubricant additives, to the production of the novel compounds, and to the lubricants containing them.

Various additives are in general added to mineral and synthetic lubricants in order to improve the performance characteristics of these lubricants. There is in particular a need for additives able to protect the devices to be lubricated from frictional wear. The requirement which wear inhibitors of this kind have to meet is that they increase the load-bearing capacity of the lubricants and do not have a corrosive action on the metal parts to be protected. Phenol-containing dithiophosphates as lubricant additives have been described in the U.S. Pat. No. 3,017,422, in the G.B. Pat. No. 1,506,917 and in the U.S. Pat. No. 3,745,148. These however do not satisfy, or only partially satisfy, the strict requirements which a high-pressure antiwear additive has to meet.

There has now been found a class of phenol-containing dithiophosphates in which the dithiophosphate part is linked in a quite specific manner to the phenolic molecule. These compounds impart to lubricants, in addition to having therein a good anti-oxidation and anti-corrosion action, excellent extreme pressure and antiwear properties. Furthermore, the novel compounds are characterised by negligible formation of sediment and by no formation of ash.

The novel compounds correspond to the general formula I

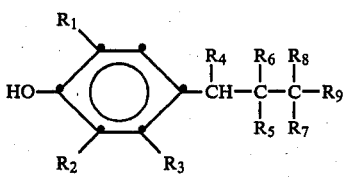

wherein $R_1$ and $R_2$ independently of one another are each $C_1$–$C_{12}$-alkyl, or they are phenyl, $C_7$–$C_9$-aralkyl or $C_5$–$C_7$-cycloalkyl each of which is unsubstituted or substituted by 1 to 3 alkyl groups having a total of 1 to 12 C atoms, $R_2$ in addition being hydrogen or chlorine, $R_3$ is hydrogen or methyl, $R_4$, $R_6$ and $R_8$ independently of one another are each hydrogen or $C_1$–$C_{20}$-alkyl, with the proviso that $R_4$, $R_6$ and $R_8$ as alkyl groups contain all together 1 to 20 C atoms, $R_9$ is hydrogen, methyl or halogen, and one of the radicals $R_5$ and $R_7$ is a group of the formula II

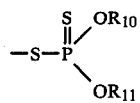

and the other is hydrogen, wherein $R_{10}$ and $R_{11}$ independently of one another are each $C_1$–$C_{30}$-alkyl or $C_2$–$C_{10}$-alkoxyalkyl, or $R_{10}$ and $R_{11}$ together are a group of the formula III

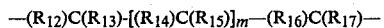

wherein m is nought or 1, and $R_{12}$, $R_{13}$, $R_{14}$, $R_{15}$, $R_{16}$ and $R_{17}$ independently of one another are each hydrogen or methyl.

$R_1$ and $R_2$ as $C_1$–$C_{12}$-alkyl are for example: methyl, ethyl, isopropyl, sec-butyl, tert-butyl, tert-amyl, n-hexyl, 1,1,3,3-tetramethylbutyl or 1,1,3,3,5,5-hexamethylhexyl. Preferred alkyl groups have 1 to 8 C atoms. In preferred compounds, $R_1$ is also tert-butyl, tert-amyl or 1,1,3,3-tetramethylbutyl.

When $R_1$ and $R_2$ are $C_7$–$C_9$-aralkyl, they can be benzyl, α-phenylethyl or α,α-dimethylbenzyl.

Where $R_1$ and $R_2$ are $C_5$–$C_7$-cycloalkyl, they can be cyclopentyl, cyclohexyl or cycloheptyl.

$R_1$ and $R_2$ as phenyl, aralkyl and cycloalkyl can be substituted with 1 to 3 alkyl groups having all together 1 to 12 C atoms. Examples of alkyl substituents of this kind are methyl, ethyl, isopropyl, n-butyl, sec-butyl, tert-butyl, n-hexyl, 1,1,3,3-tetramethylbutyl, n-nonyl, 1,1,3,3,5,5-hexamethylhexyl or n-dodecyl.

The preferred meaning of $R_3$ is hydrogen.

$R_4$, $R_6$ and $R_8$ as $C_1$–$C_{20}$-alkyl are for example methyl, ethyl, isopropyl, sec-butyl, n-hexyl, 2,2,4,4-tetramethylpentyl, straight-chain or branched-chain dodecyl, tetradecyl, octadecyl or eicosyl. Preferred alkyl groups have 1 to 6 C atoms; particularly preferred are ethyl groups and especially methyl groups. $R_9$ as halogen is in particular chlorine.

The sum of the C atoms contained in the substituents has to be in all 1 to 20, preferably 1 to 6, and in particular 1 and 2. Among the most important compounds of the formula I are those wherein one of the radicals $R_4$, $R_6$ and $R_8$ is hydrogen, and the other two are methyl; also those in which two of the radicals $R_4$, $R_6$ and $R_8$ are hydrogen, and the third is methyl; and finally those in which $R_4$, $R_6$ and $R_8$ are each hydrogen.

When $R_{10}$ and $R_{11}$ are $C_1$–$C_{30}$-alkyl, they can be for example: methyl, ethyl, n-propyl, isopropyl, n-butyl, sec-butyl, tert-butyl, n-hexyl, n-octyl, 2-ethylhexyl, 6-methylheptyl, n-octyl or straight-chain or branched-chain nonyl, decyl, dodecyl, tridecyl, tetradecyl, octadecyl, eicosyl, docosyl, tetracosyl or triacontyl. Long-chain alkyl groups consist in general of isomeric mixtures.

When $R_{10}$ and $R_{11}$ are $C_2$–$C_{10}$-alkoxyalkyl, the alkyl moiety can contain 1 to 3 C atoms and the alkoxy moiety 1 to 8 C atoms, such as in methoxymethyl, ethoxymethyl, 2-methoxyethyl, 2-ethoxyethyl, 2-n-butoxyethyl, 3-n-butoxypropyl, 2-octoxyethyl or methoxypropyl.

When $R_{10}$ and $R_{11}$ together are an alkylene group of the formula V, it is for example alkylene-1,2, such as 1-methylethylene-1,2, 1,1-dimethylethylene-1,2, 1,1,2-trimethylethylene-1,2, 1,1,2,2-tetramethylethylene-1,2, propylene-1,3, 1-methylpropylene-1,3, 1,1,3-trimethylpropylene-1,3 or 2,2-dimethylpropylene-1,3.

Preferred compounds correspond to the formula I wherein $R_1$ and $R_2$ independently of one another are $C_1$–$C_8$-alkyl, and $R_2$ is in addition hydrogen, $R_3$ is hydrogen or methyl, $R_4$, $R_6$ and $R_8$ independently of one another are each hydrogen or $C_1$–$C_6$-alkyl, with the proviso that $R_4$, $R_6$ and $R_8$ as alkyl groups have all together 1 to 6 C atoms, $R_9$ is hydrogen, and one of the radicals $R_5$ and $R_7$ is a group of the formula II and the other is hydrogen, wherein $R_{10}$ and $R_{11}$ independently of one another are each $C_1$–$C_{22}$-alkyl, or $R_{10}$ and $R_{11}$ together are a group of the formula III wherein m and $R_{12}$ to $R_{17}$ have the meanings defined above.

Particularly preferred compounds correspond to the formula I wherein $R_1$ is tert-butyl, tert-amyl or 1,1,3,3-tetramethylbutyl, $R_2$ is $C_1$-$C_8$-alkyl, $R_3$ is hydrogen, $R_4$, $R_6$ and $R_8$ independently of one another are each hydrogen, methyl or ethyl, with the proviso that $R_4$, $R_6$ and $R_8$ as alkyl groups have 1 to 2 C atoms, $R_9$ is hydrogen, and one of the radicals $R_5$ and $R_7$ is a group of the formula II and the other is hydrogen, whereby $R_{10}$ and $R_{11}$ independently of one another are each $C_1$-$C_{22}$-alkyl, or together are a group of the formula III, wherein m and $R_{12}$ to $R_{17}$ have the meanings defined above.

Typical representatives of the class of substances according to the invention are for example:

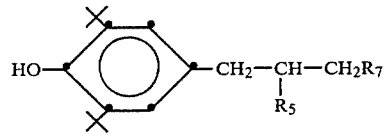

(IV)

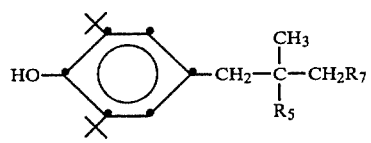

(V)

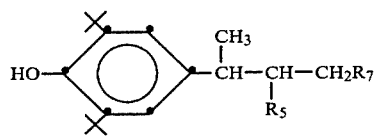

(VI)

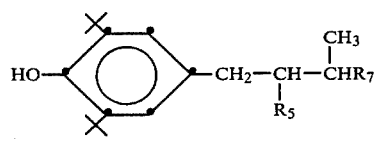

(VII)

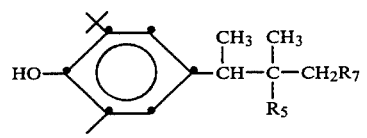

(VIII)

In the formulae IV to VIII, one of the radicals $R_5$ and $R_7$ is hydrogen, and the other is a group of the formula II wherein $R_{10}$ and $R_{11}$ have the following meanings:

| No. | $R_{10}$ | $R_{11}$ |
|---|---|---|
| IV-VIII 1.a/b | isopropyl | isopropyl |
| IV-VIII 2.a/b | 2-ethylhexyl | 2-ethylhexyl |
| IV-VIII 3.a/b | methyl | methyl |
| IV-VIII 4.a/b | octadecyl | n-butyl |
| IV-VIII 5.a/b | docosyl | docosyl |
| IV-VIII 6.a/b | tridecyl | tridecyl |

| No. | $R_{10} + R_{11}$ | |
|---|---|---|
| IV-VIII 7.a/b | 1,1,3-trimethylpropylene-1,3 | |
| IV-VIII 8.a/b | 2,2-dimethylpropylene-1,3 | |
| IV-VIII 9.a/b | ethylene-1,2 | |

As compounds (a) are denoted those in which $R_5$ is hydrogen, and $R_7$ is a group of the formula II in which $R_{10}$ and $R_{11}$ have the meanings given in the Table. As compounds (b) are denoted those in which $R_5$ is a group of the formula II wherein $R_{10}$ and $R_{11}$ have the given meanings, and $R_7$ is hydrogen.

The compounds of the formula I are produced in a manner known per se, for example by the addition reaction of a compound of the formula IX

(IX)

wherein $R_{10}$ and $R_{11}$ have the meanings defined above, with an alkene of the formula X

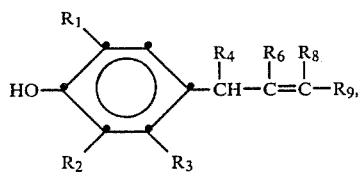

(X)

wherein the symbols $R_1$, $R_2$, $R_3$, $R_4$, $R_6$, $R_8$ and $R_9$ have the meanings defined above.

The addition reaction can be performed in an inert solvent or preferably without solvent at temperatures of 0°–180° C., particularly 50°–150° C., and optionally in the presence of a radical initiator.

Suitable solvents are optionally chlorinated, aliphatic or aromatic hydrocarbons, such as special grades of petroleum spirit, or hexane, heptane, methylene chloride, 1,2-dichloroethane, benzene, chlorobenzene, dichlorobenzene, toluene or xylene; or ethers, such as diethyl ether, dioxane or tetrahydrofuran.

Radical initiators usable for the radically catalysed addition reaction are for example in particular: peroxy and azo compounds, as well as UV light. Customary peroxy compounds are hydrogen peroxide, di-t-butyl peroxide, cumene hydroperoxide or dibenzoyl peroxide. A suitable azo compound is especially $\alpha,\alpha'$-azodiisobutyric acid nitrile.

There is obtained by the addition reaction described, besides the compound of the formula I in which $R_5$ is hydrogen and $R_7$ is a group of the formula II, as a rule the isomeric compound of the formula I in which $R_5$ is a group of the formula II and $R_7$ is hydrogen. The separation of the isomers is performed in a known manner. Usually however the isomeric mixture is used directly for the application as lubricant additives.

The compounds of the formula IX are known compounds and are readily available commercially.

The compounds of the formula X are likewise known, or, in cases where they are new, they can be produced in a known manner. One method for producing them is described for example in the U.S. Pat. No. 3,526,668.

Even in very small amounts, the compounds of the formula I are effective as high-pressure additives in lubricants. Thus, mineral and synthetic lubricating oils, and also mixtures thereof, which contain 0.001 to 5 percent by weight, preferably 0.02 to 3 percent by weight, relative to the lubricant, of a compound of the formula I display excellent high-pressure lubricating properties which are clearly manifested in greatly reduced wear phenomena on the parts in contact which have been lubricated. The lubricants which can be used are commonly known to those skilled in the art, and are described for example in "Schmiermittel Taschenbuch"

["Lubricants Handbook"](Hüthig Verlag, Heidelberg, 1974).

The lubricating-oil formulation can additionally contain other additives which are added in order to improve certain basic oil properties, additives such as antioxidants, metal passivators, rust inhibitors, agents for improving the viscosity index, pour-point depressors, dispersants/detergents and other additives which protect against wear.

Examples of antioxidants are:
(a) alkylated and non-alkylated aromatic amines and mixtures thereof, for example: dioctyldiphenylamine, mono-t-octylphenyl-α- and -β-naphthylamines, phenothiazine, dioctylphenothiazine, phenyl-α-naphthylamine and N,N'-di-sec-butyl-p-phenylenediamine;
(b) sterically hindered phenols, for example 2,6-di-tert-butyl-p-cresol, 4,4'-bis-(2,6-diisopropylphenol), 2,4,6-triisopropylphenol, 2,2'-thio-bis-(4-methyl-6-tert-butylphenol) and 4,4'-methylene-bis-(2,6-di-tert-butylphenol);
(c) alkyl phosphites, aryl phosphites or aralkyl phosphites, for example: trinonyl phosphite, triphenyl phosphite and diphenyldecyl phosphite;
(d) esters of thiodipropionic acid or thiodiacetic acid, for example: dilauryl thiodipropionate or dioctyl thiodiacetate;
(e) salts of carbamic and dithiophosphoric acids, for example: antimony diamyldithiocarbamate and zinc diamyldithiophosphate; and
(f) combinations of two or more antioxidants from the above, for example: an alkylated amine and a sterically hindered phenol.

Examples of metal passivators are:
(a) for copper, for example: benzotriazole, tetrahydrobenzotriazole, 2-mercaptobenzothiazole, 2,5-dimercaptothiadiazole, salicylidene-propylenediamine and salts of salicylaminoguanidine;
(b) for lead, for example: sebacic acid derivatives, quinizarine and propyl gallate; and
(c) a combination of two or more of the above additives.

Examples of rust inhibitors are:
(a) organic acids and their esters, metal salts and anhydrides, for example: N-oleoyl-sarcosine, sorbitane monooleate, lead naphthenate and dodecenylsuccinic anhydride;
(b) nitrogen-containing compounds, for example:
I. primary, secondary or tertiary aliphatic or cycloaliphatic amines and amine salts of organic and inorganic acids, for example oil-soluble alkyl-ammonium carboxylates, and
II. heterocyclic compounds, for example: substituted imidazolines and oxazolines;
(c) phosphorus-containing compounds, for example: amine salts of phosphoric acid partial esters;
(d) sulfur-containing compounds, for example: barium dinonylnaphthalene-sulfonates and calcium petroleum sulfonates; and
(e) combinations of two or more of the above additives.

Examples of agents which improve the viscosity index are: polymethacrylates, vinylpyrrolidone/methacrylate copolymers, polybutenes, olefine copolymers and styrene/acrylate copolymers.

Examples of pour-point depressors are: polymethacrylates and alkylated naphthalene derivatives.

Examples of dispersants/detergents are: polybutenylsuccinic acid imides, polybutenylphosphonic acid derivatives and hyperbasic sulfonates and phenolates of magnesium, calcium and barium.

Examples of other additives which provide protection against wear are: compounds which contain sulfur and/or phosphorus and/or halogen, such as vegetable oils treated with sulfur, zinc dialkyldithiophosphates, tritolyl phosphates, chlorinated paraffins, alkyl disulfides and aryl disulfides.

The Examples which follow further illustrate the invention.

EXAMPLE 1

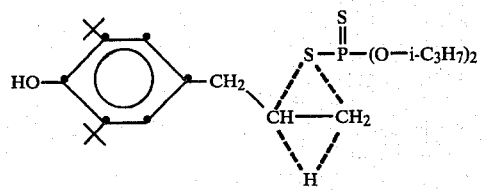

214 g of dithiophosphoric acid-O,O-diisopropyl ester are added under nitrogen to 246 g of 3-(3,5-di-t-butyl-4-hydroxyphenyl)-prop-1-ene, and with the addition of 1 g of azodiisobutyric acid nitrile in several portions the mixture is heated, with stirring, for 8–10 hours at 90°–110° C. At the end of the reaction period, there is practically no further olefin detectable (thin-layer chromatography).

The substance is freed in vacuo (~15 mm Hg/80° C.) from readily volatile impurities. The isomeric mixture thus obtained forms a slightly brownish viscous oil, and can be used directly for application according to the invention as a lubricant additive.

EXAMPLE 2

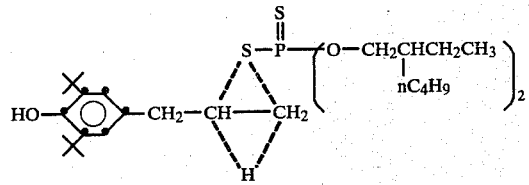

By replacing the diisopropyl ester of Example 1 by the corresponding amount of dithiophosphoric acid-di-2-ethyl-n-hexyl ester, with otherwise the same procedure, there is obtained the above isomeric mixture in the form of a viscous, almost colourless oil.

EXAMPLE 3

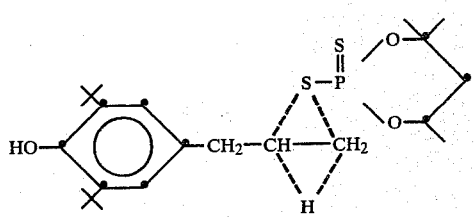

With use of the corresponding cyclic O,O-diester of dithiophosphoric acid with 1,1,3-trimethyl-1,3-dihydroxypropane, there is obtained, analogously to Example 1, the above-given isomeric mixture in the form of a viscous, almost colourless oil.

EXAMPLE 4

The following values were determined using the Shell four-ball apparatus (Tentative method IP 239/69, extreme pressure and wear lubricant test for oils and greases, four-ball machine).

TABLE (1) I.S.L. = Initial Seizure Load: that is the load under which the oil film breaks down within a duration of load application of 10 seconds.

(2) W.L. = Weld Load: that is the load under which the 4 balls weld together within 10 seconds.

(3) W.S.D. = Wear Scar Diameter in mm: that is the mean wear diameter when a load of 40 kg is applied for 1 hour.
Vitrea 41 (Shell trade name) was used as the base oil.
Concentration of the stabiliser: 1 percent by weight.

| Stabiliser | ISL (kg) | WL (kg) | WSD (mm) |
|---|---|---|---|
| none | about 60 | about 160 | about 2.4 |
| Example 1 | 100 | 240 | 0.4 |
| Example 2 | 100 | 220 | 0.4 |

EXAMPLE 5

Oil-oxidation test, standard version according to ASTM D 2272 (Rotary Bomb Oxidation Test)

An oil specimen of 50 ml of mineral oil, "Vitrea 41" (Shell trade name), with the addition of 0.25 g of stabiliser is oxidised, in a glass vessel, together with 5 ml of distilled water and a polished, catalytically acting copper coil, which has been washed with petroleum ether, in an oxygen atmosphere. The glass vessel is in a stainless-steel bomb fitted with a pressure gauge. The bomb rotates axially at 100 r.p.m., at an angle of 30° with the horizontal, in an oil bath at 150° C. Before heating commences, the oxygen pressure is initially about 6 atm. (90 psi); it increases at 150° C. to nearly 14 atm. (200 psi) and then remains constant until oxidation occurs. The test is terminated with a drop in pressure of 1.7 atm. (25 psi), and the time in minutes until that occurs is recorded.

| Stabiliser | Test results: Minutes until pressure drop of 25 psi occurs |
|---|---|
| none | 16 |
| Example 1 | 193 |
| Example 2 | 120 |

EXAMPLE 6

Oil-oxidation test according to IP 280, "CIGRE"

Modified version with soluble Cu and Fe catalyst.
Conditions: Introduction of oxygen for 4 hours at 150° C. (4 liters of O₂/h).
Determination of the acid number after end of test; table value: mg KOH consumption per gram of test oil.
Stabiliser concentration: 0.5 percent by weight.
Test oil: mineral oil "Vitrea 41" (Shell trade name).

TABLE

| Stabiliser | mg KOH/g |
|---|---|
| none | 3.6 |
| Example 1 | 1.45 |
| Example 2 | 1.22 |

What is claimed is:

1. A compound of formula I

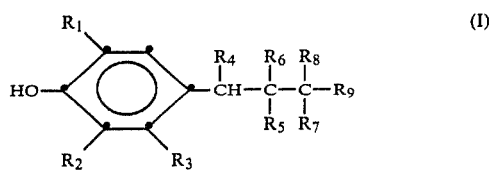

wherein $R_1$ and $R_2$ independently of one another are each $C_1$–$C_8$-alkyl, and $R_2$ in addition is hydrogen, $R_3$ is hydrogen or methyl, $R_4$, $R_6$ and $R_8$ independently of one another are each hydrogen or $C_1$–$C_6$-alkyl, with the proviso that $R_4$, $R_6$ and $R_8$ as alkyl groups have all together 1 to 6 C atoms, $R_9$ is hydrogen and one of the radicals $R_5$ and $R_7$ is a group of the formula II

and the other is hydrogen, wherein $R_{10}$ and $R_{11}$ independently of one another are each $C_1$–$C_{22}$-alkyl, or $R_{10}$ and $R_{11}$ together are a group of the formula III

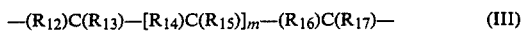

wherein m is nought or 1, and $R_{12}$, $R_{13}$, $R_{14}$, $R_{15}$, $R_{16}$ and $R_{17}$ independently of one another are each hydrogen or methyl.

2. A lubricant composition comprising a mineral or synthetic lubricating oil or mixture of said oils, and from 0.001 to 5% by weight, relevant to the oil, of a compound of formula I according to claim 1.

3. A compound according to claim 1 of the formula I wherein $R_1$ is tert-butyl, tert-amyl or 1,1,3,3-tetramethylbutyl, $R_2$ is $C_1$–$C_8$-alkyl, $R_3$ is hydrogen, $R_4$, $R_6$ and $R_8$ independently of one another are each hydrogen, methyl or ethyl, with the proviso that $R_4$, $R_6$ and $R_8$ as alkyl groups have 1 to 2 C atoms, $R_9$ is hydrogen, and one of the radicals $R_5$ and $R_7$ is a group of the formula II and the other is hydrogen, whereby $R_{10}$ and $R_{11}$ independently of one another are each $C_1$–$C_{22}$-alkyl, or together are a group of the formula III, wherein m and $R_{12}$ to $R_{17}$ have the meanings defined in claim 1.

4. A compound according to claim 1 of the formula I wherein two of the radicals $R_4$, $R_6$ and $R_8$ are hydrogen, and the third is methyl.

5. A compound according to claim 1 of the formula I wherein one of the radicals $R_4$, $R_6$ and $R_8$ is hydrogen, and the other two are methyl.

6. A compound according to claim 4 of the formula I wherein $R_4$ is methyl, and $R_6$ and $R_8$ are hydrogen.

7. A compound according to claim 4 of the formula I wherein $R_6$ is methyl, and $R_4$ and $R_8$ are hydrogen.

8. A compound according to claim 4 of the formula I wherein $R_8$ is methyl, and $R_4$ and $R_6$ are hydrogen.

9. A compound according to claim 1 which is

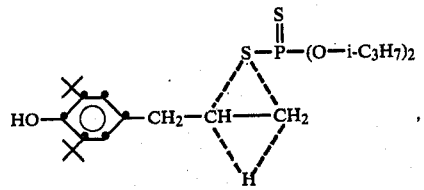
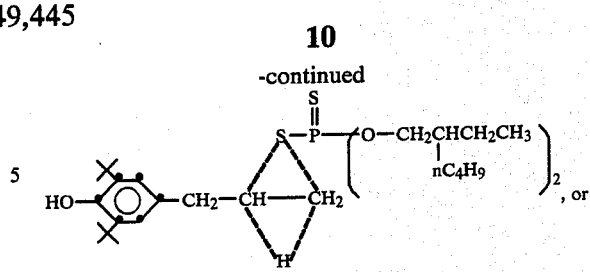
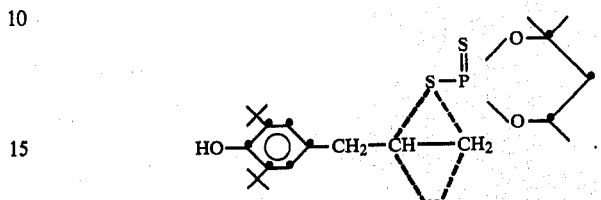
* * * * *